(12) United States Patent
Buschbell et al.

(10) Patent No.: US 10,706,486 B2
(45) Date of Patent: Jul. 7, 2020

(54) SYSTEM FOR DETERMINING USER-CENTRIC TREATMENT DATA

(71) Applicant: Fresenius Medical Care Deutschland GmbH, Bad Homburg (DE)

(72) Inventors: Jörg Buschbell, Friedrichsdorf (DE); Luca Gialdini, Lodi (IT); Carlo Barbieri, Crema (IT); Flavio Mari, Crema (IT); Wolfgang Wehmeyer, Tübingen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 225 days.

(21) Appl. No.: 15/632,823

(22) Filed: Jun. 26, 2017

(65) Prior Publication Data

US 2018/0012322 A1  Jan. 11, 2018

(30) Foreign Application Priority Data

Jul. 8, 2016  (EP) ..................................... 16178574

(51) Int. Cl.
*G06Q 50/24* (2012.01)
*G06F 16/48* (2019.01)
*G16H 40/20* (2018.01)
*G06Q 10/10* (2012.01)
*H04L 9/32* (2006.01)

(52) U.S. Cl.
CPC ........... *G06Q 50/24* (2013.01); *G06F 16/489* (2019.01); *G06Q 10/1091* (2013.01); *G16H 40/20* (2018.01); *H04L 9/3228* (2013.01)

(58) Field of Classification Search
CPC .... G16H 40/20; G16H 10/60; G06Q 10/1091; G06Q 50/24
See application file for complete search history.

(56) References Cited

U.S. PATENT DOCUMENTS

2005/0209886 A1* 9/2005 Corkern ................. G06Q 50/22
                                                                 705/2
2006/0220798 A1* 10/2006 Willis ................ G08B 21/0492
                                                             340/286.07

(Continued)

OTHER PUBLICATIONS

European Patent Application No. 16 178 574.6, Office Action (dated Oct. 22, 2019).

*Primary Examiner* — Michael J Dalbo
(74) *Attorney, Agent, or Firm* — Leydig, Voit & Mayer, Ltd.

(57) ABSTRACT

A system relating to medical treatment, such as hemodialysis or peritoneal dialysis, for determining user-centric treatment data includes a user device and a central device. The user device and the central device each include a wireless communication component. The wireless communication component of the central device and/or the wireless communication component of the user device is/are configured to distinguish between the user device being in a first location and the user device being in a second location, wherein the first location is associated with a treatment area and the second location is associated with a general purpose area. The user device and/or the central device is configured to determine, based on the user device being in the first location and/or the user device being in the second location, an overall treatment time and an overall spent time.

15 Claims, 3 Drawing Sheets

(56) References Cited

U.S. PATENT DOCUMENTS

| | | | |
|---|---|---|---|
| 2006/0273883 A1* | 12/2006 | Pillai | G06K 7/0008 340/10.42 |
| 2010/0324922 A1* | 12/2010 | Kendall | G06Q 10/10 705/2 |
| 2012/0278134 A1* | 11/2012 | Papay | G06Q 10/06375 705/7.37 |
| 2013/0325508 A1 | 12/2013 | Johnson et al. | |
| 2014/0135588 A1* | 5/2014 | Al-Ali | G16H 40/63 600/300 |
| 2014/0229099 A1* | 8/2014 | Garrett | G06Q 10/063114 701/465 |
| 2016/0180045 A1 | 6/2016 | Syed | |
| 2017/0124526 A1* | 5/2017 | Sanderford | G06Q 10/1095 |
| 2017/0161442 A1* | 6/2017 | Runci | G01S 5/10 |
| 2018/0130554 A1* | 5/2018 | Cheng | G16H 40/20 |

* cited by examiner

SYSTEM FOR DETERMINING USER-CENTRIC TREATMENT DATA

CROSS-REFERENCE TO RELATED APPLICATIONS

Priority is claimed to European Patent Application No. EP 16178574.6, filed on Jul. 8, 2016, the entire disclosure of which is hereby incorporated by reference herein.

BACKGROUND

In the medical field it is important to provide a most complete documentation of any data acquired allowing for diagnosis.

Therefore, a plurality of systems have been proposed in the past allowing a healthcare professional to enter data or to store acquired data in a patient-specific file. In such an approach, a workstation at any appropriate room (e.g. doctor's office, ultrasonic room) within a healthcare center is typically provided where a healthcare provider or its personnel in general may enter/retrieve data relating to a specific patient. This approach may be more precisely described as a healthcare professional-centric system as the focus is directed to the healthcare professional's needs.

The main purpose of data management is to facilitate maximizing asset utilization efficiency and billing to the healthcare systems. In analogy to a production line, the patient information in this system is "raw material," which can be stored and processed during the process. Cost for storage is marginal compared to asset underutilization cost, since patients' opportunity cost of idle time is not charged to the healthcare provider. This cost is covered partially by the patient and his or her employer, depending on status.

With the advent of platforms allowing for documenting patients' satisfaction either for purpose of their healthcare insurance and/or for public sharing, a growing attention may be perceived to better understand issues to improve in order to increase patients' satisfaction.

A key element in patients' satisfaction and thereby also in the outcome of any treatment involved with a patient's visit to a healthcare provider is that a patient perceives that his or her visit is effective as well. Patients' satisfaction is therefore also linked to the outcome of a treatment, such that an improved satisfaction also increases measurable positive results due to treatment. This increased level of well-being will also lead to reduced healthcare costs.

Therefore, there is a need to improve patient satisfaction.

SUMMARY

Exemplary embodiments of the invention provide a system relating to medical treatment, such as hemodialysis or peritoneal dialysis, for determining user-centric treatment data. The system, for example, may include a user device and a central device, wherein the user device and the central device each include a wireless communication component. The wireless communication component of the central device and/or the wireless communication component of the user device is/are configured to distinguish between the user device being in a first location and the user device being in a second location, wherein the first location is associated with a treatment area and the second location is associated with a general purpose area. The user device and/or the central device is configured to determine, based on the user device being in the first location and/or the user device being in the second location, an overall treatment time and an overall spent time.

BRIEF DESCRIPTION OF THE FIGURES

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
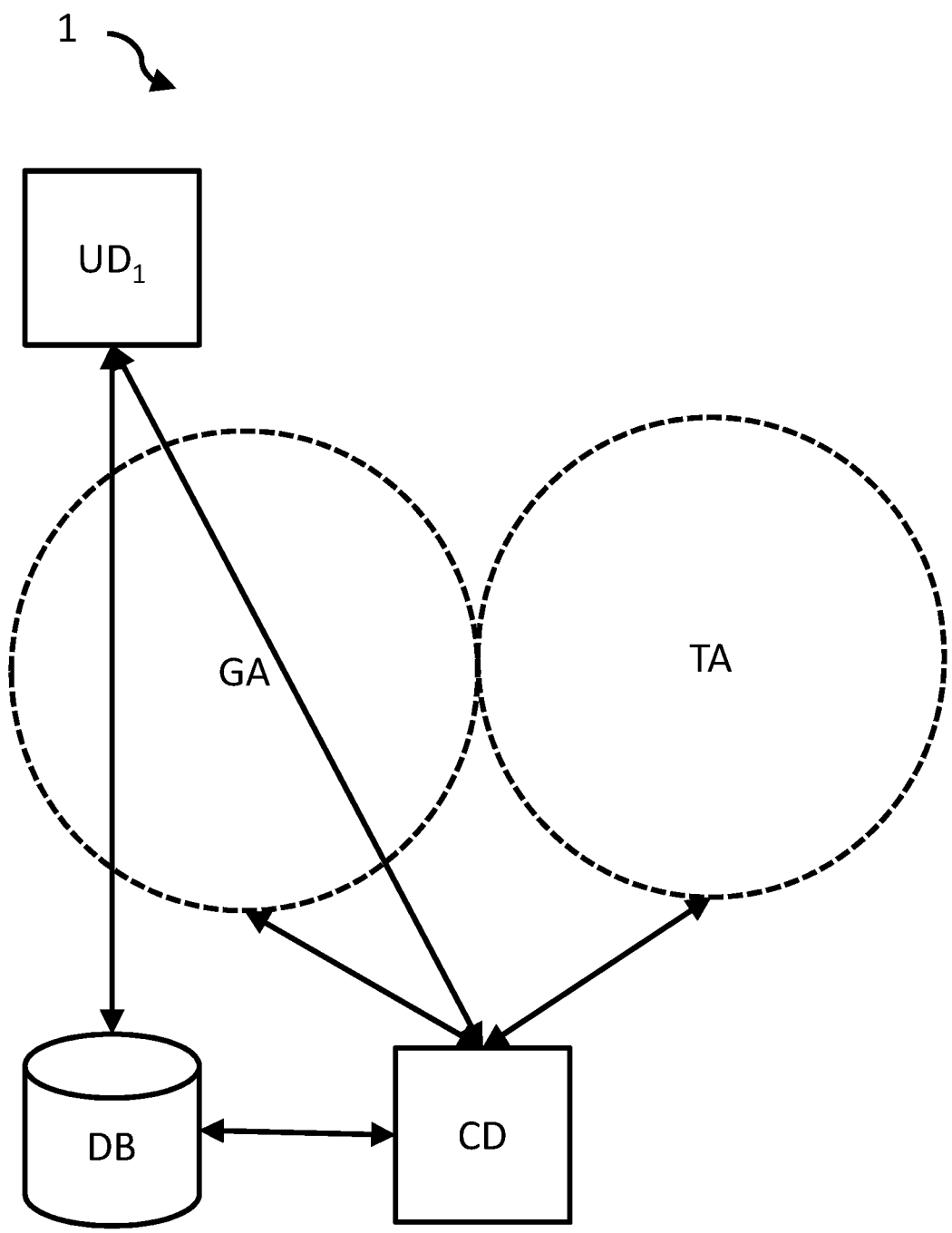
FIG. 1 shows a schematic overview according to several aspects of the invention.

Exemplary embodiments of the invention provide a system for determining user-centric treatment data, comprising a user device and a central device, whereby the user device and the central device each comprise a wireless communication component, whereby either the communication component of the central device is able to distinguish at least two different locations of user device or the wireless communication component of the user device is able to distinguish at least two different locations of the user device, whereby a first location is associated with a treatment area and a second location is associated with a general purpose area, whereby the system determines based on the distinguished locations an overall treatment time and an overall spent time.

Exemplary embodiments of the invention thus provide for knowing time periods spent for a visit to a healthcare provider and being able to distinguish whether a certain time period was spent due to waiting time or treatment time or time necessary to perform further investigations such as processing of samples. By knowing the times spent it is possible to improve the processing such that the patients' experience and thereby the patients' satisfaction is improved.

According to an embodiment of the invention the wireless communications components are near-field communication components.

Typical user devices having near-field communication components such as smartphones may be employed such that the system may be easily deployed.

According to another embodiment of the invention the wireless communications components conform to a Bluetooth standard.

The Bluetooth standard is a widespread near-field communication standard which may also be used in connection with other devices used in the medical field such as heart rate sensors and the like. Hence, as already today a number of devices are equipped with Bluetooth the systems may be easily deployed.

According to yet another embodiment a user-specific token is exchanged by the user device and the central device.

A user-specific token allows for easy tracking of a patient.

In yet another embodiment the user-specific token is generated by the central device.

This allows for easy processing.

According to a further embodiment of the invention an overall treatment time is started after exchange of the user token.

Storing overall treatment time allows for an easy determination of a metric which may be employed for improving patients' satisfaction.

In yet a further embodiment user-specific data is provided by the user device towards the central device.

User-specific data allows for storing not only time stamps but also for gathering further details allowing for a more complete analysis.

According to a further embodiment an overall treatment time is started after user-specific data is provided by the user.

Hence, the user itself may control whether the process is started or not.

According to yet another embodiment overall treatment time and overall spent time is stored in a database.

Storing times allows for gathering data not only of a single patient but to evaluate a plurality of records on different time periods (e.g. on a day-by-day basis, on a treatment basis, on an hourly basis, etc.). Hence, evaluation may be versatile to detect, for example, problems associated with a single treatment, a certain time of day, etc.

According to a still further embodiment of the invention generalized overall treatment time and generalized overall spent time is made available via an Internet interface, such as a web site or application interface.

The present disclosure describes preferred embodiments with reference to the Figures, in which like reference signs represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, refer to the same embodiment.

The described features, structures, or characteristics of the invention may be combined in any suitable manner in one or more embodiments. In the description, numerous specific details are recited to provide a thorough understanding of embodiments of the invention.

Unless indicated as alternative only, any feature of an embodiment may also be utilized in another embodiment.

In addition, even though at some occurrences certain features will be described with reference to a single entity, such a description is for illustrative purpose only and actual implantations of the invention may also comprise one or more of these entities. Usage of a singular representation also encompasses plural entities unless otherwise indicated.

Figure 3:
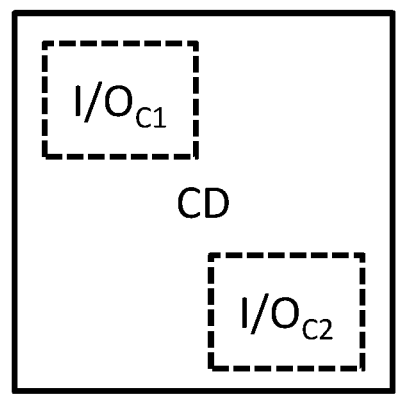
FIG. 3 shows a schematic overview of a central device according to an aspect of the invention.
Figure 4:
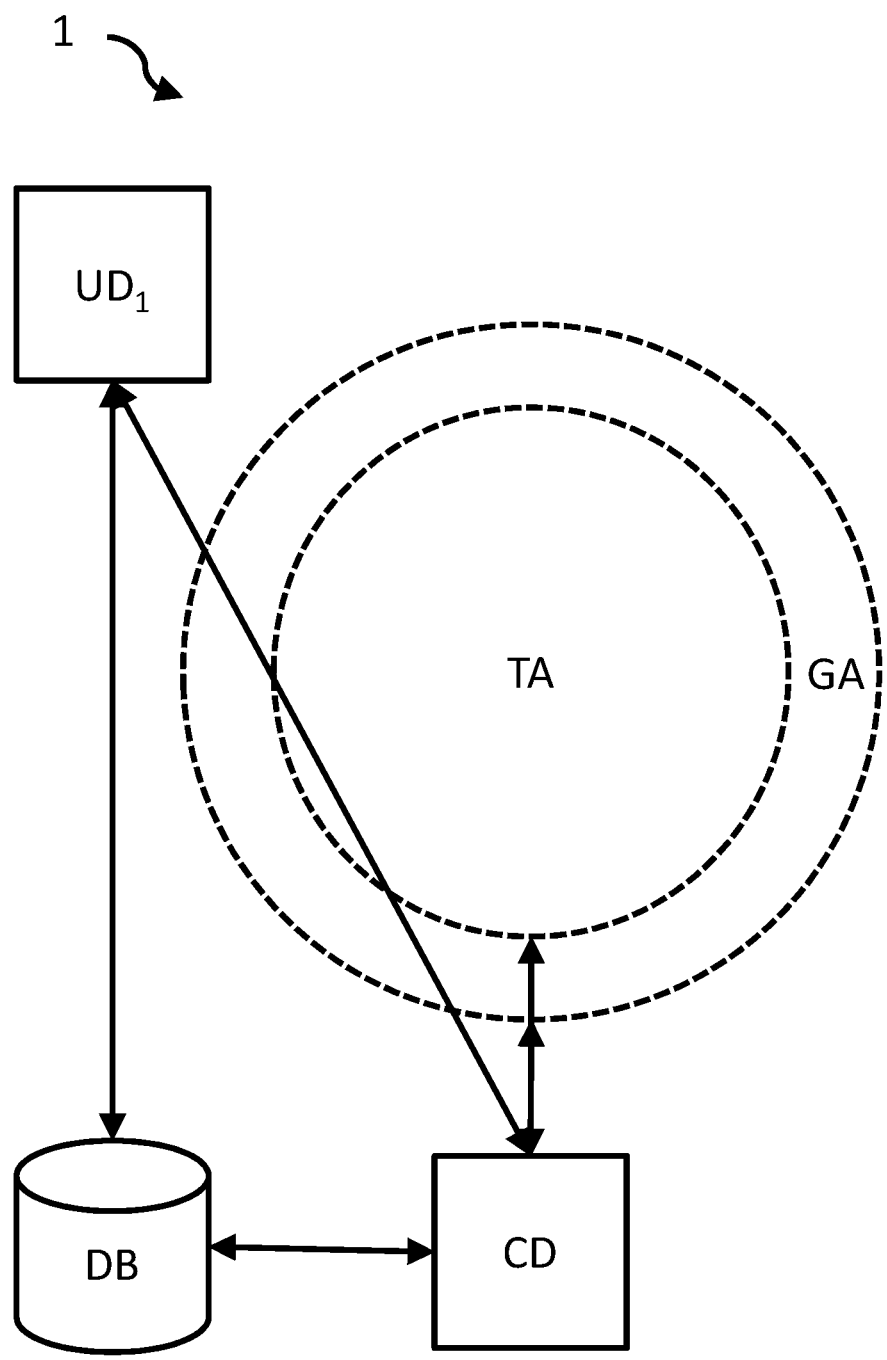
FIG. 4 shows another aspect of the invention.

In FIG. 1 and FIG. 4, a schematic overview according to several aspects of the invention is shown. There a system 1 for determining user-centric treatment data is shown. The system 1 comprises a user device $UD_1$ which is further detailed in FIG. 2 and a central device CD which is further detailed in FIG. 3. Information accessed and stored by the components of the system described herein may be accessible from and stored in a database DB.

It is noted that the invention is not limited to a single user device $UD_1$ but may be used with a plurality of user devices. Also the terminology of central device CD does not exclude the central device CD from being implemented as a distributed apparatus. For ease of understanding, the system components are described with respect to a user device and a central device.

In an exemplary embodiment, the user device $UD_1$ and the central device CD comprise wireless communication components $I/O_U$, $I/O_{C1}$. These wireless communication components are configured such that the central device CD and the user device $UD_1$ may communicate with each other.

Furthermore, either the wireless communication component $I/O_{C1}$ of the central device CD is able to distinguish at least two different locations of user device $UD_1$ and/or the wireless communication component $I/O_U$ of the user device $UD_1$ is able to distinguish at least two different locations of the user device $UD_1$ relative to the central device CD, whereby a first location is associated with a treatment area (TA) and a second location is associated with a general purpose area (GA). In various embodiments, the treatment area TA may be located remotely from the general purpose area GA (see, e.g., FIG. 1) or the treatment area TA may be located within the general purpose area GA (see, e.g., FIG. 4).

This set-up allows for a user-centric data acquisition and determination as well as a centralized data acquisition.

The determination may be performed in a number of ways, examples of which are provided below.

A first approach may be to provide a plurality of wireless communication components $I/O_{C1}$, $I/OC_2$ at various places (see FIG. 3), such that approaching the wireless communication components $I/O_{C1}$, $I/O_{C2}$ may be detected and logged. Due to a location mapping each wireless communication component $I/O_{C1}$, $I/O_{C2}$ may be associated with a certain place and consequently with a certain time attribution. For example, once a patient enters or leaves a doctor's office is registered with wireless communication component $I/O_{C1}$, and/or once a patient enters or leaves a waiting area of the doctors' office the patient is registered with wireless communication component $I/O_{C1}$, and/or once a patient enters or leaves a treatment/examination area of the doctor's office is registered with wireless communication component $I/O_{C2}$.

In another exemplary embodiment, for example when the general purpose area and the treatment area TA are overlapping as shown in FIG. 4, further data available within (short range) wireless communication systems available and allowing for determining a distance/location may be used to detect a patient's location. Such features may comprise signal strength detected, time of flight, etc.

Figure 2:
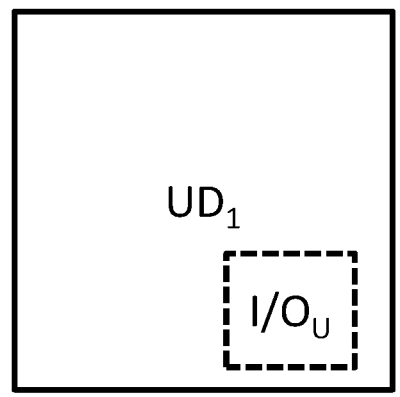
FIG. 2 shows a schematic overview of a user device according to an aspect of the invention.

Note, although the devices of FIG. 2 and FIG. 3 may be understood as a single device, the drawings only show that certain functionality is associated with a certain entity. While some sort of integration may be envisaged, the system allows for a distributed approach.

Such approaches may also be combined and may allow for triangulation to more precisely determine a patient's location.

The system 1 determines, based on the distinguished locations, an overall treatment time and an overall spent time.

Knowing time periods spent with a visit to a healthcare provider and being able to distinguish whether a certain time period was spent due to waiting time or treatment time or time necessary to perform further investigations such as processing of samples is advantageous. By knowing the times spent it is possible to improve the processing such that the patients' experience and thereby patients' satisfaction is improved.

According to an embodiment of the invention the wireless communications components $I/O_{C1}$, $I/O_{C2}$, $I/O_U$ are near-field communication components.

This allows for an easy deployment of the system as these types of communication components are already in widespread use.

According to an embodiment of the invention the wireless communications components conform to a Bluetooth standard.

The Bluetooth standard is a widespread near-field communication standard which may also be used in connection with other devices used in the medical field such as heart rate sensors and the like. Hence, as already today a number of devices are equipped with Bluetooth the systems may easily be deployed. Due to the nature of near-field communication technology, granularity may be improved allowing for precise localization as well as reduced interference.

Bluetooth, like any other true near-field communication system, may allow for communication within a room and/or a rather limited distance in the range of some amount of meters.

In a further embodiment of the invention a user-specific token is exchanged by the user device and the central device.

Exchange of a user-specific token allows for easy control by the patient as well as by the healthcare provider. Thereby, it may also be ensured that the systems allow for a true patient determination rather than a device determination.

In yet another embodiment the user-specific token is generated by the central device.

This allows for easy administration and for easy (post-) processing.

In a further embodiment of the invention an overall treatment time is started after exchange of the user-specific token.

Storing overall treatment time allows for an easy determination of a metric which may be employed for improving patients' satisfaction.

In yet a further embodiment of the invention user-specific data is provided by the user device towards the central device.

User-specific data allows for storing not only time stamps but also for gathering further details allowing for a more complete analysis.

According to a further embodiment an overall treatment time is started after user-specific data is provided by the user.

Hence, the user itself may control whether the process is started or not.

According to yet another embodiment overall treatment time and overall spent time is stored in database.

Storing times allows for gathering data not only of a single patient but to evaluate a plurality of records on different time periods (e.g. on a day-by-day basis, on a treatment basis, on an hourly basis, etc.). Hence, evaluation may be versatile to detect, for example, problems associated with a single treatment, a certain time of day, etc.

According to a still further embodiment of the invention generalized overall treatment time and generalized overall spent time is made available via an Internet interface, such as a web site or an application interface.

In general the invention allows for patient-centric data acquisition such that, for example, a time spent by a patient on treatments performed on the patient as well as the waiting time spent by the patient is acquired. The system allows for creating a quality metric from the viewpoint of the patient, the quality metric including treatment time of a patient and waiting time of a patient.

Via wireless communication devices, the location of patient may be established without needing further interaction.

It is noted that for example by offering Internet access via the same wireless communications components $I/O_{C1}$, $I/O_{C2}$ to patients one could easily reuse existing infrastructure. On the other hand a healthcare provider may easily gather patients' satisfaction data without excessive investment.

It is to be noted, the evaluation may be done at any appropriate device which may include the central device CD itself (e.g. illustrated in example by the connection between CD and database DB) or any other device which may access the acquired data. While an evaluation of data at a user device $UD_1$ is not excluded and may, for example, be provided for data related to a user (e.g. illustrated in example by the connection between $UD_1$ and database DB), it is foreseen that evaluation may be provided by the healthcare provider or a service provider for the healthcare provider.

As noted above, a token may be generated. Such a token may be patient- and/or treatment-specific. This token may be generated either by the user device $UD_1$, by the central device CD, or by a third-party device (e.g. a service provider for the healthcare provider). It may also be envisaged that a token pair is generated. Once a patient reaches a healthcare provider and the token(s) is/are exchanged, a patient is registered at a specific location (e.g. a treatment location, a waiting area, etc.).

Alternatively and/or in addition to the token approach described above user data may be exchanged by the wireless communication components. As such any kind of data allowing for user identification may be exchanged, including name, social security number, ID card number, driver's license number, etc.

While a registration on physical properties of a network interface such as a media access control (MAC) address allows for an identification of user devices, this may turn out as insufficient in case a user device is used by different persons.

Hence, even though a wireless communication component $I/O_{C1}$ may start registration of time spent upon entering within the reach of a wireless communication device, it may be more precise to start time recording by pairing the devices with additional data to be exchanged.

The system 1 that is described allows for automatic recording of the point in time when a physician or nurse sees a patient and starts treatment at a Start Time of Service (STS). This information may be acquired by a mobile device of the patient. The mobile device may be, for example, any kind of smartphone or smart device (such as a tablet, a smartwatch, etc.) and may be equipped with an application adapted for exchange of user data and/or tokens.

At a time—preferably around a scheduled appointment—the mobile device $UD_1$ with an app is (constantly/periodically) searching for an identifier from a sender signal from a physician or nurse (e.g., from a central device CD in a near field network). If detected (e.g. for a threshold time which makes the start of treatment plausible), the time of first recognition is recorded.

When the mobile device loses its connection (e.g. for more than a defined threshold time), an End Time of Service (ETS) is recorded.

This approach allows for a user device-centric approach as well as a central device-centric approach as well as third party-centric approach as well as mixtures thereof.

In an exemplary implementation, with a user device-centric approach, it is the user device which detects arrival and/or departure relative to wireless communication components $I/O_{C1}$, $I/O_{C2}$ of the central device CD. It is to be noted that the wireless communication components of the central device may also be embodied by mobile devices associated with a specific person. For example, a nurse and/or a doctor may also be equipped with a smartphone or a tablet being provided with a respective wireless communication component.

Exemplary embodiments of the invention allow for smooth integration into existing systems as well as for requiring minimal or no interaction.

Examples of data that can be determined allowing for determination of a patient satisfaction will be discussed in further detail below.

For example, exemplary embodiments of the invention may be utilized to determine the following metrics indicative of a patient's satisfaction:
waiting time start treatment (STS—scheduled time)
total physician time TPhT (ETS—STS for physicians)
total nursing time TNuT (ETS—STS for nurses)
    total waiting time (last ETS—scheduled time−TNuT−TPhT)

Evaluation may be performed as indicated by any suited device including the user device $UD_1$ and the central device CD. In an exemplary embodiment, a user device may only evaluate data indicative for a respective user. The result of the determination as detailed above may be provided for further processing to other devices of the system and/or third parties.

For example, the data and/or the result of the evaluation may be provided for storage in a patient record for personal documentation, a physician's information technology (IT) system for personal documentation, and/or a database which averages the waiting of patients for the physician site, and/or for public access as overall quality data (e.g. via publishing on the Internet).

It is to be noted that when "time" is referred to in the above description, the term is not limited to a time scheme of a day but may also encompass a time indicating date as well.

Exemplary embodiments of the invention provide for making patient satisfaction metrics available for different parties. Thereby evaluation and thereupon improvement is enabled leading to increased treatment success.

Furthermore, the system according to exemplary embodiments of the invention allows patients to compare results of different practitioners in a precise, reliable and transparent manner.

It will be appreciated by those of skill in the art that the execution of the various machine-implemented processes and steps described herein may occur via the computerized execution of processor-executable instructions stored on a non-transitory computer-readable medium, e.g., random access memory (RAM), read-only memory (ROM), programmable read-only memory (PROM), volatile, nonvolatile, or other electronic memory mechanism. Thus, for example, the operations described herein performed by computing devices and components thereof may be carried out according to stored instructions and/or installed applications.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A system, comprising:
a plurality of mobile devices of a plurality of patients, wherein each mobile device is associated with a respective patient of the plurality of patients and wherein each mobile device comprises a respective first wireless communications component; and
a plurality of provider devices associated with a plurality of treatment providers, the plurality of provider devices comprising one or more nurse devices and one or more physician devices, wherein each nurse device and each physician device includes a respective second wireless communications component;
wherein the plurality of mobile devices and/or the plurality of provider devices are configured to determine treatment times associated with a plurality of treatments for the plurality of patients based on wireless communication between the plurality of mobile devices and the plurality of provider devices using the respective first wireless communications components and the respective second wireless communications components, wherein determining the treatment times comprises:
    determining a respective nurse Start Time of Service (STS) based on a respective nurse device coming into wireless communication range of a respective mobile device of a patient;
    determining a respective nurse End Time of Service (ETS) based on the respective nurse device leaving wireless communication range of the respective mobile device of the patient;
    determining a respective physician Start Time of Service (STS) based on a respective physician device coming into wireless communication range of the respective mobile device of the patient; and
    determining a respective physician End Time of Service (ETS) based on the respective physician device leaving wireless communication range of the respective mobile device of the patient;
wherein a provider device and/or another device is configured to analyze the treatment times associated with the plurality of treatments and output a plurality of metrics indicative of patient satisfaction, including a comparison of respective metrics associated with different providers, wherein analyzing the treatment times includes;

determining one or more treatment times based on one or more physician STSs, one or more physician ETSs, one or more nurse STSs and one more nurse ETSs; and determining an overall waiting time based on an overall spent time minus the one or more treatment times, wherein the overall spent time corresponds to a total time from a start time to a last nurse ETS or a last physician ETS.

2. The system according to claim 1, wherein the respective first wireless communications components and the respective second wireless communications components are near-field communication components.

3. The system according to claim 1, wherein the respective first wireless communications components and the respective second wireless communications components conform to a Bluetooth standard.

4. The system according to claim 1, wherein each mobile device is configured to exchange a patient-specific token with a respective provider device.

5. The system according to claim 4, wherein the patient-specific token is generated by the respective provider device.

6. The system according to claim 4, wherein exchange of the patient-specific token triggers counting of treatment time.

7. The system according to claim 1, wherein each mobile device is configured to provide patient-specific data to the plurality of provider devices.

8. The system according to claim 7, wherein provision of the patient-specific data triggers counting of treatment time.

9. The system according to claim 1, further comprising:
a database configured to store the treatment times associated with the plurality of treatments.

10. The system according to claim 1, further comprising:
an Internet interface configured to make wait time and treatment time information available via the Internet.

11. The system according to claim 1, wherein the provider device and/or another device is configured to determine problems associated with a particular treatment or associated with a certain time of day based on the analyzed treatment times associated with the plurality of treatments.

12. A system, comprising:
a mobile device of a patient, the mobile device of the patient comprising a first wireless communications component; and
a plurality of provider devices associated with a plurality of treatment providers, the plurality of provider devices comprising one or more nurse devices and one or more physician devices, wherein each nurse device and each physician device includes a respective second wireless communications component;

wherein the mobile device of the patient and/or the plurality of provider devices are configured to determine an overall wait time and an overall treatment time associated with a treatment of the patient based on a scheduled start time of the treatment and one or more time periods during which the first wireless communications component of mobile device of the patient is within wireless communication range of at least one second wireless communications component of at least one provider device;

wherein a respective nurse device coming into wireless communication range of the mobile device of the patient corresponds to a respective nurse Start Time of Service (STS), and the respective nurse device leaving wireless communication range of the mobile device of the patient corresponds to a respective nurse End Time of Service (ETS);

wherein a respective physician device coming into wireless communication range of the mobile device of the patient corresponds to a respective physician Start Time of Service (STS), and the respective physician device leaving wireless communication range of the mobile device of the patient corresponds to a respective physician End Time of Service (ETS);

wherein the overall treatment time includes: a total physician time (TPhT) based on one or more physician STSs and one or more physician ETSs; and a total nursing time (TNuT) corresponding to one or more nurse STSs and one more nurse ETSs; and wherein the overall waiting time corresponds to an overall spent time minus the overall treatment time, wherein the overall spent time corresponds to a total time from the scheduled start time of the treatment to a last nurse ETS or a last physician ETS.

13. The system according to claim 12, wherein a respective nurse device or a respective physician device is determined as having left the wireless communication range of the mobile device of the patient based on the mobile device of the patient losing a connection with the respective nurse device or the respective physician device for more than a defined threshold time.

14. The system according to claim 12, wherein the mobile device of the patient is configured to determine that a provider device is within wireless communication range of the mobile device of the patient by continuously or periodically searching for an identifier from a sender signal corresponding to a provider.

15. The system according to claim 14, wherein the mobile device of the patient is configured to begin continuously or periodically searching for the identifier around the scheduled start time of the treatment.

* * * * *